United States Patent [19]
Wuchinich

[11] Patent Number: 5,176,677
[45] Date of Patent: Jan. 5, 1993

[54] ENDOSCOPIC ULTRASONIC ROTARY ELECTRO-CAUTERIZING ASPIRATOR

[75] Inventor: David G. Wuchinich, New York, N.Y.

[73] Assignee: Sonokinetics Group, Hoboken, N.J.

[21] Appl. No.: 439,114

[22] Filed: Nov. 17, 1989

[51] Int. Cl.$^5$ .................. A61B 17/32; A61B 17/36
[52] U.S. Cl. .................. 606/46; 606/169; 606/171; 606/180; 604/22; 128/24 AA
[58] Field of Search ............... 606/46, 128, 169, 170, 606/171, 174, 180; 128/24 AA; 604/22

[56] References Cited

U.S. PATENT DOCUMENTS

| | | | |
|---|---|---|---|
| 2,742,076 | 4/1956 | Klein | 29/427 |
| 3,401,446 | 9/1968 | Obeda et al. | 156/344 X |
| 3,526,219 | 9/1970 | Balamuth | 128/2 |
| 3,589,363 | 6/1971 | Banko et al. | 128/276 |
| 3,614,484 | 10/1971 | Shoh | 310/8.2 |
| 3,683,736 | 8/1972 | Loose | 264/25 X |
| 3,809,977 | 5/1974 | Balamuth | 318/116 |
| 3,906,954 | 9/1975 | Baehr et al. | 604/27 |
| 4,203,444 | 5/1980 | Bonnell et al. | 128/276 |
| 4,223,676 | 9/1980 | Wuchinich et al. | 128/276 |
| 4,316,465 | 2/1982 | Dotson, Jr. | 604/22 |
| 4,428,748 | 1/1984 | Peyman et al. | 604/22 |
| 4,504,264 | 3/1985 | Kelman | 604/22 |
| 4,609,368 | 9/1986 | Dotson, Jr. | 604/22 |
| 4,643,717 | 2/1987 | Cook et al. | 604/22 |
| 4,732,156 | 3/1988 | Nakamura | 128/660 |
| 4,747,820 | 5/1988 | Hornlein et al. | 604/22 |
| 4,748,985 | 6/1988 | Nagasaki | 128/660 |
| 4,750,488 | 6/1988 | Wuchinich et al. | 128/303 R |
| 4,750,902 | 6/1988 | Wuchinich et al. | 604/22 |
| 4,756,304 | 7/1988 | Sachse et al. | 606/180 X |
| 4,828,052 | 5/1989 | Duran et al. | 175/55 |
| 4,834,102 | 5/1989 | Schwarzchild et al. | 128/662.06 |
| 4,838,853 | 6/1989 | Parisi | 604/22 |
| 4,846,790 | 7/1989 | Hornlein et al. | 604/22 |
| 4,880,011 | 11/1989 | Imade et al. | 128/662.06 |
| 4,881,761 | 11/1989 | Hornlein et al. | 285/239 |
| 4,936,281 | 6/1990 | Stasz | 128/660.3 |
| 4,979,952 | 12/1990 | Kubota et al. | 606/169 |

FOREIGN PATENT DOCUMENTS 203229 10/1983 German Democratic Rep. .

OTHER PUBLICATIONS

Krawitt et al., Ultrasonic Aspiration of Prostate, Bladder Tumors and Stones, *Urology*, 30:6 (1987) pp. 578–580.
Richmond et al., Evaluation of the Histopathology of Brain Tumor Tissue Obtained by Ultrasonic Aspiration, *Neurosurgery*, 13:4 (1983), pp. 415–419.
Malloy et al., Endoscopis Ultrasonic Aspiration of the Prostate, Bladder Tumors and Stones, Journal of Urology Supplement, May 1989.
Epstein et al., Surgical Management of Extensive Intramedullary Spinal Cord Astrocytoma in Children, Concepts in Pediatric Neurosurgery, 2, (1982) pp. 29–44.
Sternlieb et al., Ultrasonic Restoration of Severly Calcified Aortic Valve, *The Lancet*, Aug. 20, 1988, p. 446.
Caspar, Current Development of Instrumentation for Arthroscopy, *Clinics in Sports Medicine*, 6:3 (1987), pp. 626–627.
Johnson, Arthroscopic Surgery:Principles and Practice (3rd Edition), Verlag Springer (1986), pp. 244–245.
Brochure, Endo-Urology-A Breakthrough in Ultrasonic Lithotripsy, Karl Storz Endoscopy-America, Inc. (1984).
Brochure, Instruments and Apparatus for Lithotripsy, Richard Wolf GmbH, Knittlinger, West Germany (1984).
Brochure, Percutaneous Low Pressure Universal Nephroscope, Richard Wolf, Knittlinger, West Germany (1984).

*Primary Examiner*—Lee S. Cohen
*Assistant Examiner*—Kevin Pontius
*Attorney, Agent, or Firm*—Pennie & Edmonds

[57] ABSTRACT

A surgical instrument having a handpiece; a vibration source within the handpiece for generating mechanical vibrations in response to current supplied thereto; an elongated tool operatively associated with the vibration source and attached to the handpiece at a point where essentially no vibrational motion occurs; the tool extending away from the handpiece to a work site, whereby vibration of the working tip of the tool causes disintegration of hydrated biological material; a motor oberatively associated with the vibration source for rotating the tool and its working tip about its circumference through at least one revolution; a support structure located within the handpiece for mounting said vibration source and capable of independent longitudinal movement relative to the handpiece; a fingergrip for longitudinally reciprocating the support structure and tool towards and away from the work site independently of moving the handpiece; an open portion for irrigating the work site with fluid to assist in withdrawing removed biological material therefrom; and an aspiration system for withdrawing irrigation fluid and removed biological material from the work site. This instrument may also include a telescope for use as an endoscopic ultrasonic aspirator.

26 Claims, 10 Drawing Sheets

FIG. 6A1 Prior Art
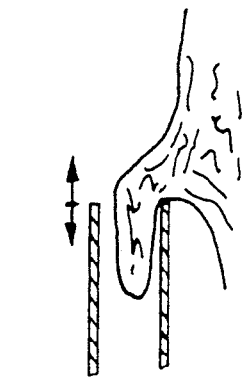
FIG. 6A2 Prior Art
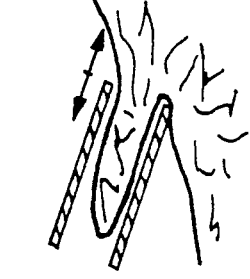
FIG. 6A3 Prior Art
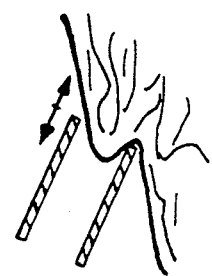
FIG. 6A4 Prior Art
FIG. 6B1
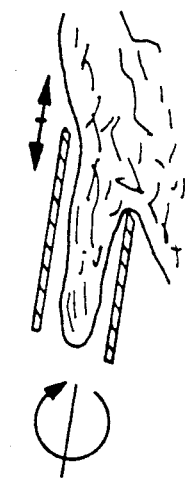
FIG. 6B2
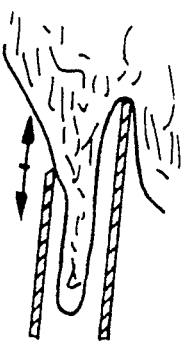
FIG. 6B3
FIG. 6B4
New Invention

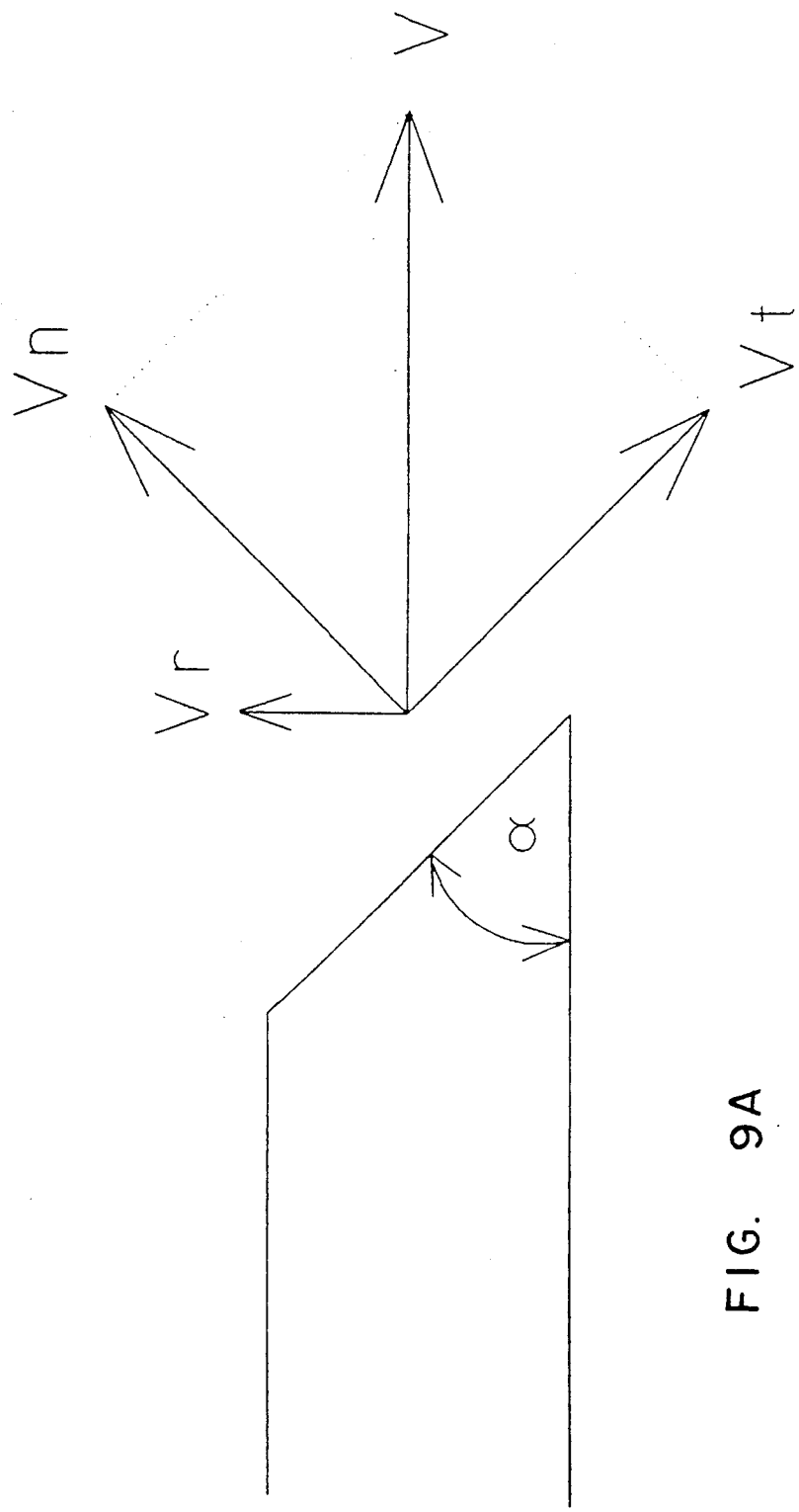

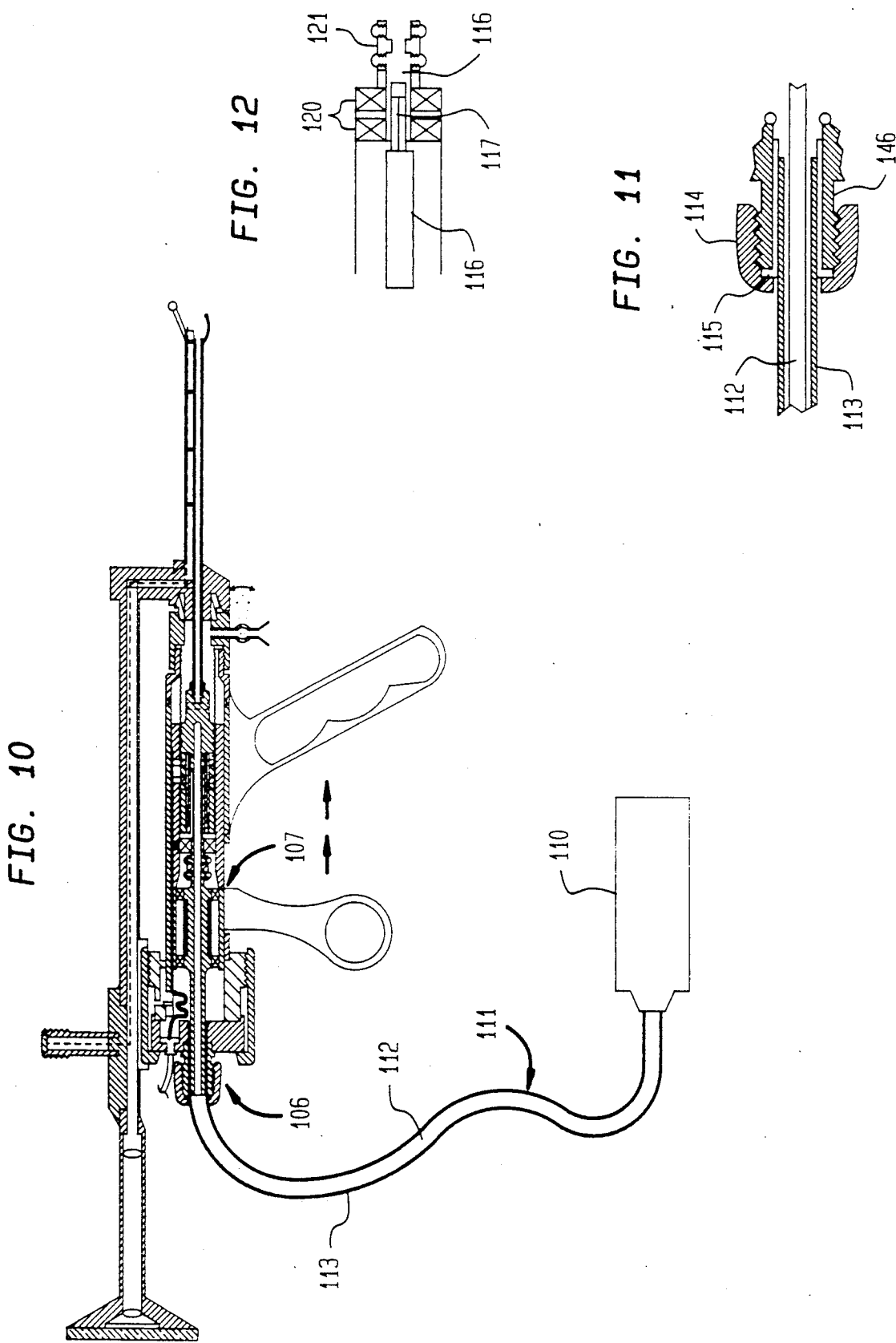

ENDOSCOPIC ULTRASONIC ROTARY ELECTRO-CAUTERIZING ASPIRATOR

TECHNICAL FIELD

The present invention relates to surgical instruments; in particular to an endoscopic aspirator which utilizes ultrasonic vibration and a rotating tip to dissect and remove tissue, while also being capable of imparting reciprocal linear movement and electro-cauterizing current to the tip for enhanced tissue removal.

BACKGROUND ART

The use of ultrasonic aspiration equipment for surgical procedures is well known in the art. U.S. Pat. No. 3,589,363 disclose ultrasonic aspiration for use in removing cataracts. U.S. Pat. No. 4,223,676 relates to its use for the removal of neoplastic tissue and U.S. Pat. No. 4,750,902 includes endoscopic procedures for bladder tumor and stone removal.

These devices have proven to provide great utility in medical surgical practice. Soft tissue is athermally dissected, leaving parent tissue undamaged. Necrosis, common to cryosurgical, electro-surgical and laser procedures is minimized in ultrasonic surgery because cell destruction is confined to a single layer. Elastic, connective tissue, however, is resistant to ultrasonic attack. For example, blood vessels having diameters larger than 1 millimeter are normally not severed by ultrasonic aspirators. In prostatectomies, the benign gland can be entirely removed without effect to the prostatic capsule (Krawitt et al., Ultrasonic Aspiration of Prostate, Bladder Tumors and Stones, *Urology*, 30:6 (1987) pp. 578-580). Tumors of the spinal cord can also be dissected and aspirated while preserving the anatomical and physiological integrity of adjacent neural tissue. Histologic assays of ultrasonically aspirated tissue have shown preservation of cellular morphology, enabling pathological analysis of specimens to be made with confidence (Richmond et al., Evaluation of the Histopathology of Brain Tumor Tissue Obtained by Ultrasonic Aspiration, *Neurosurgery*, 13:4 (1983), pp. 415-419).

As a result of the advantages attendant to the ultrasonic technique, subjects receiving such procedures have reported more rapid recovery and better retention of normal function than populations receiving conventional treatment (Malloy et al., Endoscopic Ultrasonic Aspiration of the Prostate, Bladder Tumors and Stones, Journal of Urology Supplement, May, 1989). In some cases, such as the surgical management of astrocytomas, ultrasonic aspiration is the only known method for removal that is both safe and effective (Epstein et al., Surgical Management of Extensive Intramedullary Spinal Cord Astrocytoma in Children, *Concepts in Pediatric Neurosurgery*, 2, (1982) pp. 29-44). The application of this technology, initially in ophthalmic and neurosurgery, has consequently grown to embrace urologic, general and cardiovascular surgery, where, recently, the successful debridement of calcified heart valves has been demonstrated (Sternlieb et al., Ultrasonic Restoration of Severely Calcified Aortic Valve, *The Lancet*, Aug. 20, 1988, p. 446).

U.S. Pat. No. 4,750,902 includes a comprehensive review of the art and literature forming the foundation of the technology. In essentially all indicated applications, the instrumentation excites and sustains controlled extensional resonance of slender, hollow, prismatic tubes, thereby producing a standing wave whose principal attribute of interest is reciprocal motion of a surgical tip. The frequency of vibration, determined by the dimensions of the tube and the electro-mechanical transducer exciting the motion, is typically selected to lie within the range of 10 to 50 kHz (10,000 to 50,000 cycles of vibration per second). It has been discovered that, if the magnitude of the vibration is adequately large within this frequency band, the application of the tip directly to soft tissue, such as muscle, produces separation of the cellular structure at the locus of contact. The peak to peak vibration amplitude required to produce the phenomena depends upon the particular tissue under consideration, but usually lies within the range of 6 to 18 mils (0.006 to 0.018 inches or 150 to $460 \times 10^{-6}$ m). If a source of vacuum is simultaneously applied to the bore of the hollow tip, tissue parted by the vibration can be separated and withdrawn into a suitable collection vessel.

The agent responsible for the observed phenomena is cavitation of intercellular water, or the free water between cells. Cavitation is well known for causing the erosion of apparatus such as ship propellers for example. Cavitation may also be used to advantage in ultrasonic cleaning apparatus. In surgical applications, the free intercellular water enters a vapor phase, manifest as micron ($10^{-6}$ m) sized bubbles, as the tip rapidly retracts during one half cycle of vibration. When the tip returns in the next half cycle, the bubbles collapse, producing extraordinarily high but very localized pressure. Typically, the pressures produced are on the order of one million atmospheres. Cell walls adjacent to the tip are ruptured in the process, producing the observed dissection.

Because the effect is greatly dependent upon free water content, ultrasonic aspiration can differentiate between tissues of different hydration. For example, tumors can be dissected directly off the carotid artery and parenchyma can be separated from the vascular web in the renal pelvis. For the same reasons, the prostate can be entirely enucleated leaving both the prostatic capsule and bladder neck intact. Connective tissue such as that composing blood vessel walls, encapsulating membranes and fascia have much lower intercellular water content than the tissues they bind or contain or to which they are otherwise attached. The distinctive ability of ultrasonic vibration to discriminate and the confinement of cell destruction to one layer have thus secured acceptance of the technology in important surgical procedures.

Although dissection and aspiration using a blunt, hollow and intensely vibrating tube have demonstrated significant surgical utility, their use is limited precisely by the very effect they exploit: tissues having little hydration are extremely resistant to attack. For example, in surgery of the knee, where the meniscus or synovium must be partially removed to restore function following an injury, this technology currently offers no competition to the scalpels or other cutting devices available to perform the procedure. The same situation prevails regarding the discs of the spinal cord. In general, within the body, those structures intended to absorb physical abuse from exertion are difficult to excise surgically. It is in these specialties of surgical practice that ultrasonic aspiration has been notably unsuccessful Another limitation of current ultrasonic instruments involves their restricted ability to cleanly dissect the "cores" of tissue that are produced from the parent structure. This difficulty is particularly noticeable when the subject anatomy is perpendicular or at an acute angle to the tip. Tissue filling the tip bore can not easily be separated without angling the tip to sever the "pedestal" attachment, and, in certain procedures, anatomical restrictions do not permit such movement. An example is the aspiration of the pituitary gland, which is located at the base of the brain. The inability of the straight ultrasonic tip to completely remove this portion of the gland through an opening made in the roof of the mouth is, in part, related to its acute presentation.

Another limitation of current ultrasonic instruments is apparent in endoscopic procedures, where the surgeon's view is provided by a telescope and where perspective is extremely important. The surgeon must be able to gauge the position of the cutting implement in relation to the entire target. The spatially fixed relation between the ultrasonic tip and telescope lens such as that disclosed in U.S. Pat. No. 4,750,902 does not provide such a perspective. A portion of the field of view is always blocked by the tip, which must, of necessity, remain visible, and it is not possible to extend the tip into the field to judge its size in relation to associated anatomy. The surgeon is thus forced to operate "right in front of his nose."

U.S. Pat. No. 3,526,219 illustrates the evident ability of ultrasonic vibration to enhance cutting by applying vibration to a number of knife tips attached to an ultrasonic transducer. In this use of vibration, cavitation plays no rule whatsoever in dissection. It is rather the addition of reciprocal motion to the blade edge that enhances penetration into tissue. However, all ultrasonic aspirators utilize a tube whose opening is at nearly a right angle to its axis and to the direction of application. If the opening is bevelled, penetration into tissue is facilitated but core pedestals remain more difficult to sever.

Also of interest to the surgeon is the possibility of providing an electrocauterizing radio frequency potential to the ultrasonic tip. The currents produced by such potentials, when passed from the tip through tissue to a return electrode, have long been known to effectively seal bleeding vessels. U.S. Pat. No. 4,750,902 discloses one way for providing such potentials to the tip of ultrasonic aspirators. Others have evaluated the use of electrical coagulating currents in the endoscopic dissection of fibrocartilaginious structures of the knee (Caspari, Current Development of Instrumentation for Arthroscopy, *Clinics in Sports Medicine*, 6:3 (1987), pp. 626–627; Johnson, Arthroscopic Surgery: Principles and Practice (third edition), Verlag Springer (1986), pp. 244–245).

U.S. Pat. No. 4,838,853 discloses an ultrasonic handpiece for the removal of meniscus. The hollow tip is vibrated extensionally while a source of vacuum is connected to the tip bore to remove dissected fragments.

U.S. Pat. No. 4,504,264 discloses an ultrasonic surgical device that provides both irrigation and aspiration as well as tip rotation through a specified arc of 5 to 60 degrees. The handpiece of this patent is rather bulky and difficult to manipulate in precise surgical procedures.

Continuously rotating instruments for the removal of tissue are also shown in U.S. Pat. No. 4,203,444, where rotation of a hollow tube within a protective sheath is used with aspiration to (1) capture tissue within a window, (2) sever the entrapped specimen by rotation of the tip and (3) withdraw the dissected tissue by vacuum to a collection container.

Rotating ultrasonic transducers are also generally known in the metal working or mineral extraction fields. U.S. Pat. No. 3,614,484 shows a method for introducing continuous rotation into an extensionally vibrating ultrasonic transducer for enhanced machining of materials. The ultrasonic transducer is mounted to the rotating, non-vibrating frame at points where significant ultrasonic vibration is known to exist. The wear induced by this support limits the life of the appliance. More recently, U.S. Pat. No. 4,828,052 shows an attachment to a rotating ultrasonic transducer that permits coaxial irrigation for the improved drilling of very hard materials.

Accordingly, there is a need in the art for a surgical instrument which is capable of reducing the disadvantages of current devices.

SUMMARY OF THE INVENTION

This invention relates to a surgical instrument comprising a handpiece; a vibration source within the handpiece for generating mechanical vibrations in response to current applied thereto; elongated tool means operatively associated with the vibration source and attached to the handpiece at a point where essentially no vibrational motion occurs and extending away from the handpiece to a work site whereby vibration of the tool means causes disintegration and removal of hydrated biological material; means for rotating the elongated tool means about its circumference through at least one revolution for enabling the elongated tool means to remove non-hydrated biological material; means for irrigating the work site with fluid to assist in withdrawing removed biological material therefrom; and aspiration means for withdrawing irrigation fluid and removed biological material from the work site.

Preferably, the elongated tool means includes a bevelled tip for providing increased shearing of biological material. Alternatively, the instrument may include a stationary sheath for surrounding the elongated tool means, wherein the sheath may include a closed tip portion having at least one aperture spaced therefrom to form a window in the sheath which facilitates further in the removal of biological material.

The instrument may also include a support structure located within the handpiece for mounting the vibration source and rotating means for independent longitudinal movement relative to the handpiece. This vibration source preferably includes a piezoelectric crystal having electrodes on inner and outer surfaces thereof; a union for connecting the crystal to the elongated tool means; and a stem extending towards the rotating means. The crystal may be tubular or in the shape of a disk. The rotating means comprises a motor for generating rotational forces and means for transmitting the forces to the vibration source stem and to the elongated tool means for rotation thereof in either clockwise or counterclockwise directions. The stem preferably has a length which is not resonant at the operating frequency of the crystal, and the elongated tool means has a length of $\Gamma/4 + n\,\Gamma/2$ where n is O or an integer and $\Gamma = c/f$ where f is the frequency of operation, c is the velocity and $\Gamma$ is the wavelength of extensional waves in the tool means.

The instrument may further comprise means for electrically insulating each of the piezoelectric crystal and the motor from the stem and union. Advantageously, the insulating means comprises ceramic spacers and means for energizing the elongated tool means may be provided to supply current for cauterizing biological material that is not removed by the instrument. The energizing means may be a spring member connected to a current source and contacting the stem through bearing means.

In another embodiment, an elongated sheath is provided for surrounding the elongated tool means. Here, the instrument advantgeously includes means for viewing the work site from the handpiece, so that the instrument can be used as an endoscopic device. The viewing means may further comprise means for illuminating the work site to facilitate viewing thereof. The viewing means may also be located within the sheath to reduce the overall size of the working end of the device. Also, the sheath may include a hood member at the forward end thereof to assist in obtaining an unobstructed view of the work site through the viewing means.

A further embodiment of the invention relates to a surgical instrument comprising a handpiece; a vibration source within the handpiece for generating mechanical vibrations in response to current supplied thereto; elongated tool means operatively associated with the vibration source and attached to the handpiece at a point where essentially no vibrational motion occurs and extending away from the handpiece to a work site whereby vibration of the tool means causes disintegration of hydrated biological material; a support structure located within the handpiece for mounting the vibration source and capable of independent longitudinal movement relative to the handpiece; means for longitudinally reciprocating the support structure and elongated tool means towards and away from the work site independently of moving the handpiece; means for irrigating the work site with fluid to assist in withdrawing removed biological material therefrom; and aspiration means for withdrawing irrigation fluid and removed biological material from the work site.

In yet another embodiment, the previously described instrument may further include means for rotation of the elongated tool means for assisting in the removal of non-hydrated biological material. In addition, electrocauterizing means and viewing means may be incorporated into this instrument, the latter to convert it to an endoscopic device.

BRIEF DESCRIPTION OF THE DRAWINGS

The invention is more fully described in connection with the attached drawing figures, wherein:

FIGS. 6A1-4 and 6B1-4 are a series of illustrations depicting tissue dissection according to the aspirator of the present invention compared to prior art devices;

FIG. 9 is a schematic of the preferred tip for the aspirator of FIG. 1 illustrating the components of velocity produced thereby;

FIG. 10 is a side view, partially in cross-section, of another endoscopic ultrasonic aspirator having a flexible shaft drive and utilizing side aspiration;

FIG. 11 is an exploded view of the flexible shaft drive for the apparatus of FIG. 10; and FIG. 12 is an exploded view of the connection of the flexible shaft drive of FIG. 11 to the apparatus of FIG. 10.

DETAILED DESCRIPTION OF THE PREFERRED EMBODIMENTS

Figure 1:
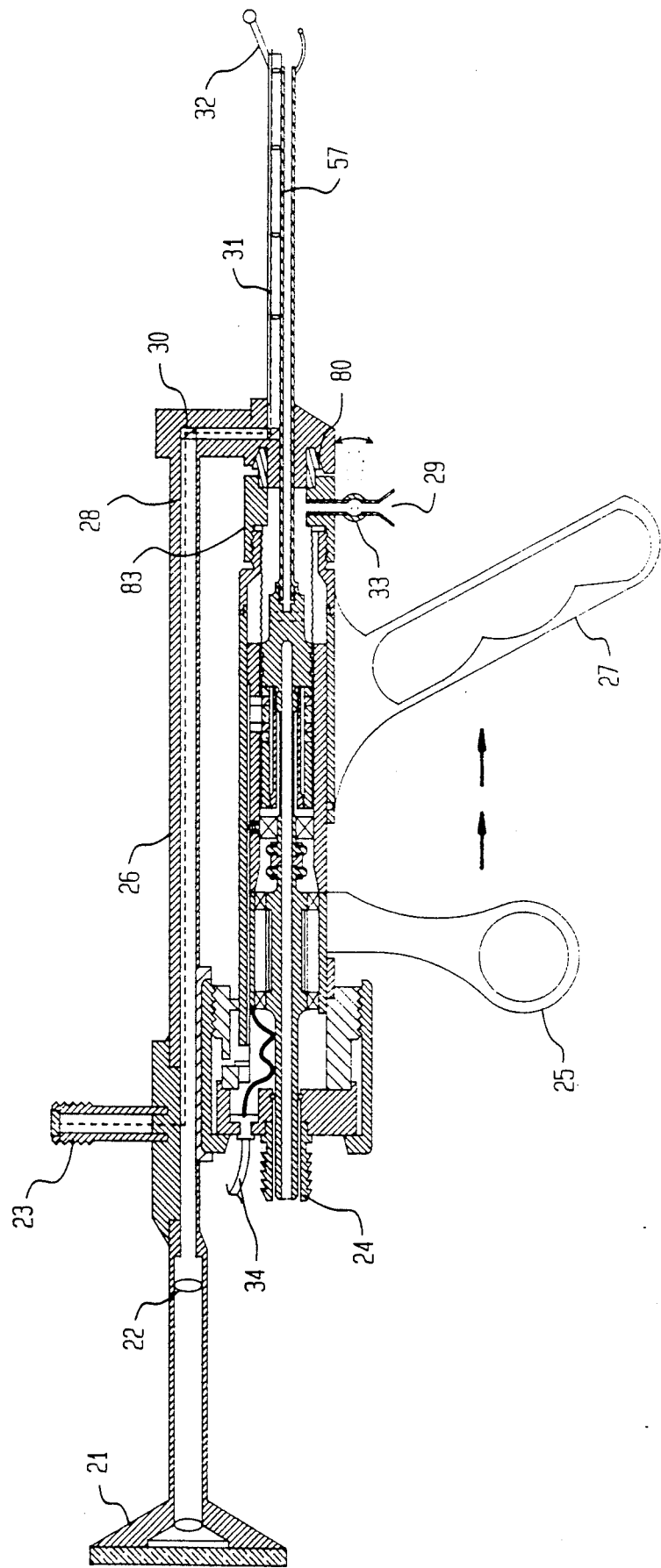
FIG. 1 is a side view, partially in cross-section, of a surgical instrument in the form of an endoscopic ultrasonic rotary electro-cauterizing aspirator according to the present invention.

FIG. 1 illustrates the surgical device of the invention in its preferred form as an endoscopic ultrasonic rotary electro-cauterizing aspirator apparatus. This apparatus includes a handpiece which houses the ultrasonic and rotational components and provides a handgrip 27 for the user, an elongated extension including a working tip 57 capable of vibrating and rotating for dissection of tissue, viewing means in the form of a telescope 21 extending form the rear of the housing to the working tip, a light source 23 for providing illumination to areas adjacent the working tip 57, an aspiration fitting 24 which communicates with the internal bore of the working tip 57; an irrigation valve 29 for introducing fluid to the working tip 57, and a thumb trigger 25 attached to the ultrasonic and rotary component support for reciprocating the working tip 57 linearly forward and backward. Each of these components is described in further detail hereinbelow.

Figure 2:
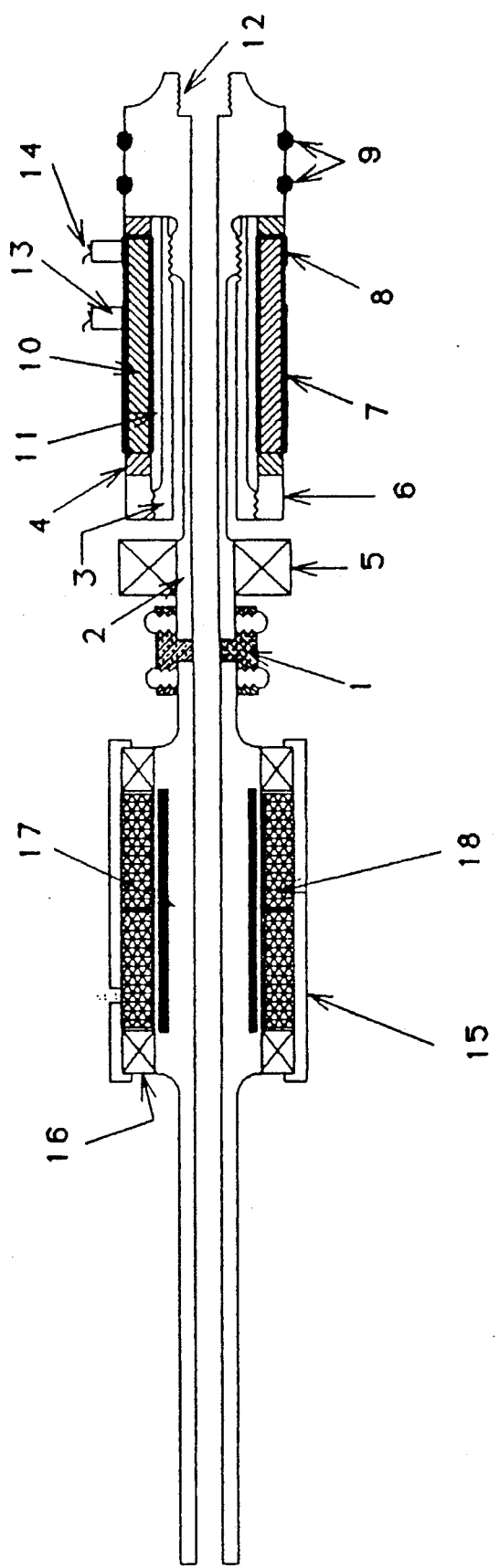
FIG. 2 is an enlarged side view, partially in cross-section, of the ultrasonic and rotational components of the aspirator of FIG. 1.

FIG. 2 shows the ultrasonic and rotational components. The ultrasonic transducer assembly includes a union 12 where the surgical tip is attached. This union is integral with a stem 2 which enters a motor coupling 1. A spindle 3 is attached to the union 12 by threads and, with the use of the prestress nut 6, holds the assembly together under the extension and contraction of vibration. Ceramic insulator rings 4 are sandwiched on each side of the tubular piezoelectric crystal 10. The crystal 10, typically made of polycrystalline zirconium titanate, contains electrodes covering its inner 8 and outer 7 surfaces, with the inner electrode wrapped around the right edge and onto the outer diameter. An electrical insulation air gap 11 separates the inner electrode from the spindle 3. Brushes 13 are held in contact with these electrodes by springs 14. In crystals of the type shown, a voltage applied between the electrodes produces a change in the axial length of the tube, thereby supplying the means for exciting vibration.

The stem 2 does not rotate so that it can be attached to a motor 15 through the insulated motor coupling 1. The motor may be any one of a number of types such as a stator winding 18 and an armature 17 which rotates. Bearings 16 support the rotation of the armature within the motor housing 15.

Insulation of the motor armature 17 and tubular piezoelectric crystal 10 from the union 12, stem 2, and spindle 3 is necessary when electrocauterizing current is to be applied independently of rotation or vibration. The radio frequency voltages normally employed in electro-cautery generators exceed 1,000 volts, a level that can easily interfere with the normal operation of motors and transducer power sources.

The insulating materials employed should have dielectric properties approaching that of a vacuum to minimize capacitive conduction of the cauterizing current, which is supplied at radio frequencies in the range of 1 MHz, into the motor and transducer assemblies. In addition, the insulator ring 4 material should have acoustic properties approaching or exceeding those of the piezoelectric material 10, since these rings are exposed to large cyclic stress at the frequency of vibration. For example, nylon may be used for the insulating material 1 of the coupling which is not subject to vibration, but a ceramic such as MACOR, which exhibits both a dielectric constant only several times that of free space and elastic losses typical of metals, is preferably used for the insulator rings 4. Exposed to the magnitude of cyclic stress generated by the transducer (i.e., about 3,000 pounds per square inch) at a frequency of 10-50 kHz, virtually all common plastics will melt or decompose.

Insulation of the piezoelectric crystal 10 from all other electrically conductive components also isolates the ultrasonic generator supply from the surgical tip 32, thereby ensuring that no unintentional currents flow through the subject. Although it is possible to isolate the ultrasonic generator from its supply of operating room utility current, the insulator rings 4 preferably afford additional and usually the desired level of protection.

The motor shown may operate as a polyphase induction machine or, with provision for a commutator on the armature shaft, as a direct current machine. If the motor is operated by alternating current, speed control is effected by a variation in the frequency and magnitude of the stator current. If the motor is a dc machine, speed control is achieved by a change in the magnitude of either or both the stator or armature currents.

The motor may also be driven by a supply of compressed gas. Where such motive power is used, the cable connecting the motor to its control and power unit contains, in addition to electrical wires for powering the transducer and electrifying the tip, flexible hoses for admitting and discharging the compressed gas. Because the instrument itself must remain sterile in use and is operated in a sterile field, spent gas exits at point remote from the handpiece.

The motor may also be located within a control and power unit and connected to the transducer stem 2 by a flexible shaft that can accommodate rotation. Such shafts are commonly available for rotating hand tools and are used extensively in such devices as automobile speedometers. Placement of the motor outside of the handpiece not only reduces the weight of the instrument, but also shortens the length of the handpiece. Both modifications assist the surgical procedure by reducing operator fatigue and improving manipulation of the apparatus. When a flexible shaft is utilized, aspiration must be implemented at another point on the handpiece to preserve sterility of dissected tissue.

Figure 4:
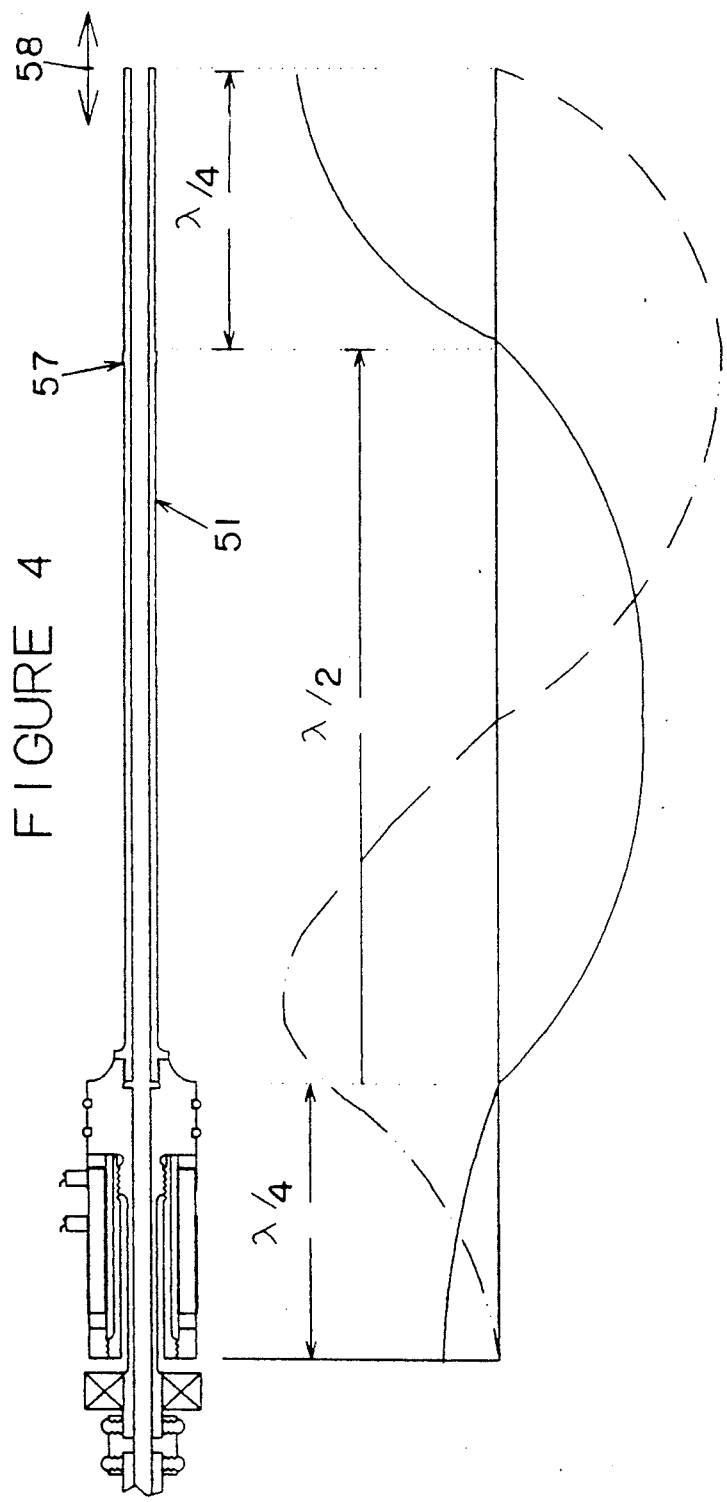
FIG. 4 is a schematic illustration of a preferred tip for the aspirator of FIG. 1 along with a stress profile along such tip.

The transducer is driven in rotation by the motor 15 through the coupling 1 and is itself supported on a bearing 5 and O-ring seals 9. Of particular interest is the form of ultrasonic motion along the transducer and tip. FIG. 4 shows both extension (peak vibration amplitude) and accompanying stress (force per unit area) within the component part of the transducer and tip 51. The direction of vibration relative to the assembly 56 is also shown. Note that the stem, which extends from the union at a point of diminished vibration, does not vibrate. The assembly of the transducer and tip are resonant as an entity at the design frequency of vibration. At points along their structure where there is little or no vibration, called the "nodes" of motion, mounting to a rigid structure such as a housing may be accomplished without impeding vibration. The magnitude of ultrasonic vibrational velocity is extremely significant. For example, a 0.001 inch peak to peak excursion at a frequency of 20 kHz has a root mean square velocity of 44 inches per second or 2.5 miles per hour. It is therefore important, if wear and the production of heat are to be minimized, that parts of the transducer in contact with stationary structures exhibit very low levels of motion. The stem, being of a length that is not resonant at the operating frequency is one such location. The O-rings on the union are another example. The raised portion of tip 57 is another node where support of the sheath can also be obtained. Note that the tip may not contact the sheath at any point other than 57 to prevent the inordinate production of heat.

The length and connection of the stem to the transducer is an important aspect of the design. Because the stem is not resonant in and of itself at the chosen operating frequency, and because it is attached to the transducer at a point of vanishing ultrasonic displacement, it has no effect upon the vibrational characteristics of the transducer and tip. Furthermore, the same reasons, the entire stem is stationary, making connection to the motor shaft possible. If, in fact, the stem length were $\Gamma/4$, where $\Gamma$ is the wavelength of extensional waves, or was, whatever its length, attached at a point on the transducer exhibiting significant ultrasonic motion, vibration would exist at the motor shaft connection, satisfactory operation could not be sustained. The motor bearing, windings and insulation would be rapidly degraded under vibration at ultrasonic frequencies. The absence of vibration on the stem also permits use of a conventional support bearing 5 for the transducer.

Although the tip is $\frac{1}{4}$ of a wavelength, $\Gamma$, long, it may be of any length that satisfies the boundary conditions: i.e., (1) vanishing motion at its point of attachment to the transducer union and (2) vanishing stress at its open end. Solution of the wave equation for a uniform prismatic tube, subject to these conditions, dictates that the tip length, L, be such that $$L = \Gamma/4 + n\Gamma/2 \tag{1}$$

where n=0 or an integer (0,1,2 ...) and $\Gamma = c/f$ where f is the frequency and c is the velocity of extensional waves in the tip.

The releasable tip is shown attached at a quarter wavelength point on the transducer so as to take advantage of the large difference in cross sectional areas between the transducer and tip to produce an increase in vibrational amplitude. It can be shown, for such a structure, that this increase or gain, G, can be expressed as $$G = (\sigma_e c_e S_e)/(\sigma_t c_t S_t) \tag{2}$$

where $\sigma$ is the density, c is the sound velocity and S is the cross sectional area. The subscript e and t refer to the effective values for the transducer and tip respectively. If this reduction in cross sectional area is not made, the motion produced by the transducer will not be sufficient to dissect tissue. Typically, piezoelectric transducers can produce about 0.001 inch peak to peak displacement at a frequency of 20 kHz. With the reduction at the $\Gamma/4$ point, the tip end displacement can easily attain 0.01 to 0.018 inch, peak to peak.

Instead of the structure shown in FIG. 2, other designs are available to produce the requisite tip excursion. The principle of quarter wavelength amplification, through a change in cross sectional area, material or both variables, is preferred for converting modest transduced displacement to levels sufficiently intense to perform the intended work.

Furthermore, although the tip is shown as a tube with uniform cross section, it is also possible to contour its shape to achieve additional motional intensity at its open end. Such alternate shapes are shown in U.S. Pat. No. 4,750,902 and are expressly incorporated herein by reference thereto. Exponential, catenoidal and gaussian tapers, subject to design at the specified frequency, therefore constitute alternative and equally useful embodiments.

Figure 3:
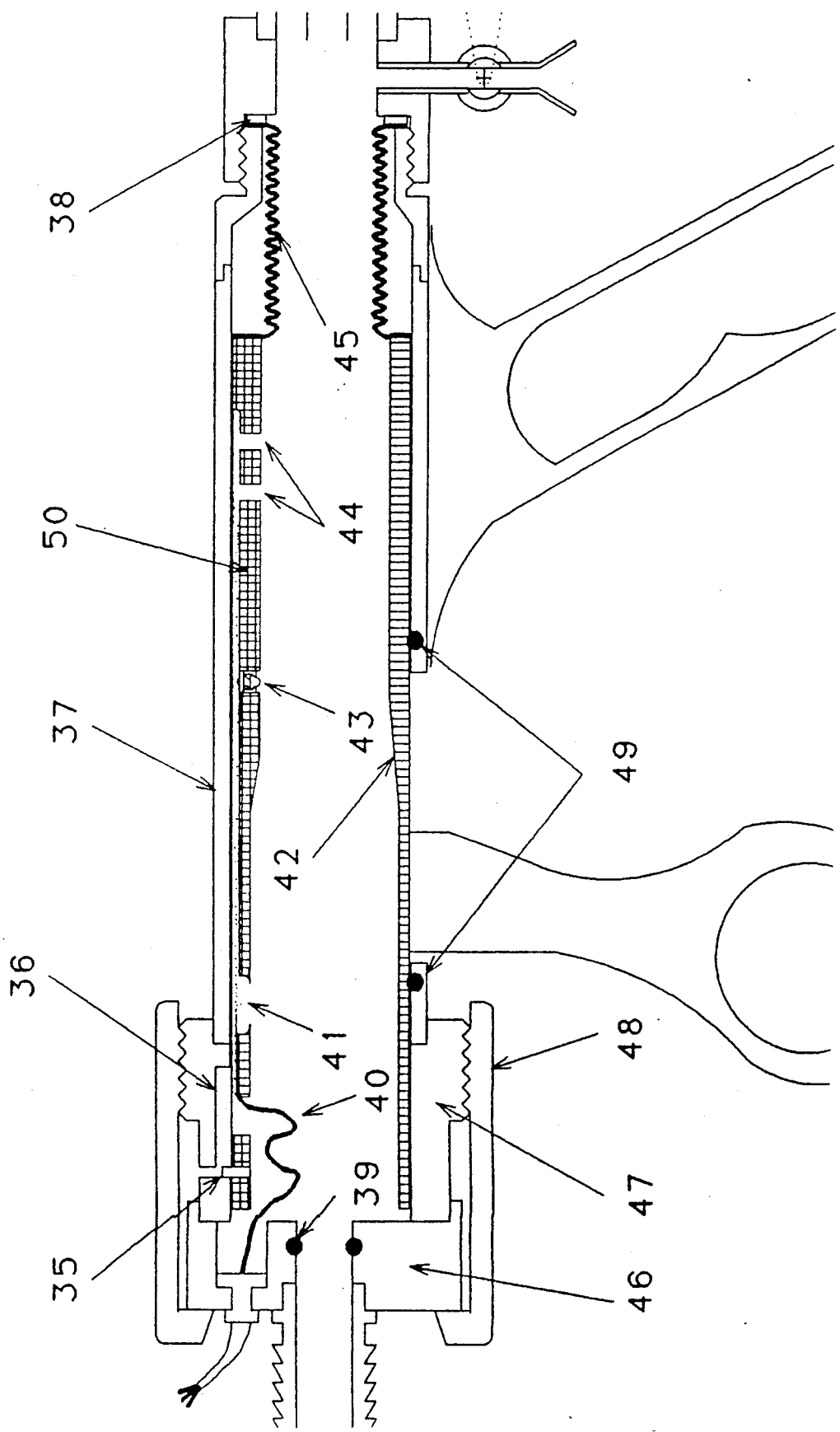
FIG. 3 is an enlarged side view, partially in cross-section, of a handpiece for the aspirator of FIG. 1.

The handpiece shown in FIG. 3 comprises both an inner moveable (but not rotatable) housing 50 and outer stationary housing 37. Cavities 44 support the transducer brushes. Spring contact 43 conveys electro-cauterizing current through bearing 5 to the stem 2 and thereby to the tip 51. The bearing is a convenient device for introducing electro-cauterizing current, but this current can also be supplied by brush contact on the stem itself or between O-rings 9 on the transducer. Entrance 41 in the inner housing is a passageway for the motor wiring. Electrical connection to the transducer brushes, bearing and motor are made to cable 40 which enters a milled channel in the linear housing.

Movement of the inner housing along the axis of the handpiece is accomplished with a moveable thumb trigger 25 attached to the inner housing and a stationary finger grip 27 connected to the outer housing. Bellows seal 45 connects the inner and outer housings, both of which do not rotate, permitting axial motion of the inner housing while preventing irrigation fluid from entering the handpiece. The transducer O-rings 9 also provide a rotating seal for preventing entry of moisture. Seal 49 is a gasket placed in a groove in the outer housing to prevent fluid from entering the housing in the vicinity of the trigger mechanism 25. This seal is of a purely sliding type.

Aspiration is performed through the stem 2, the coupling 1 and the motor armature 17. The left most portion of this armature exits the outer housing through O-ring seal 39 which again acts to exclude fluids from the handpiece. This seal is both a rotating and sliding barrier, since operation of the trigger moves the inner housing and all of its contained components.

Axial movement of the inner housing is limited by slot 36 on the outer housing and pin 35 on the inner housing, respectively. This mechanism also prevents rotation of the inner housing which would otherwise occur as a reaction to the torque of the motor armature. The rear bulkhead 46 which contains the aspiration fitting 24 and electrical cable 34 is sealed to the outer housing by nut 48 and fitting 47 which is permanently attached to outer stationary housing 37.

Although fluid seals on parts of the housing not in contact with irrigating or body fluids are not essential for operation of the instrument, they are a practical necessity. All surgical instruments must be designed to withstand sterilization by steam or immersion in room temperature cleaning or sterilizing solutions. If water vapor or solution enters the interior of the handpiece, contamination of electrical and mechanical components can place the surgeon and the patient at risk, either from electrical shock or through iatrogenic injury caused by attempts to use an improperly operating handpiece.

A medical telescope 21 may be attached to the handpiece as shown in FIG. 1. This telescope permits the surgeon to view the procedure from a point outside of the body. The telescope assembly preferably is integral with the sheath 31, and attaches to the handpiece to nut 83 with a self-locking taper fitting 80 and retaining pin 81. The optical components include the eyepiece, relay lenses 22, 28, prisms 30 as well as a fiber optic illumination cable 26 and fitting for attachment of a light source 23. An insulated hood 32, bonded to sheath 31, separates adjacent, but physically different tissues, thereby assisting the surgeon in obtaining an unobstructed view of the surgical site. The importance of this hood in obtaining a clear perspective view of the surgery, especially in tightly confining tissue cavities cannot be over-emphasized.

Irrigation is provided to the tip 57 by valve 33 which enters the outer housing and contains a luer fitting for connection to a source of fluid. It is noted that although aspiration is shown coaxially applied, it is also possible, where a motor is not provided with a hollow shaft, to aspirate through irrigation fitting 29. This can be accomplished by modifying the transducer union as discussed below with respect to the device of FIG. 8.

Figure 5:
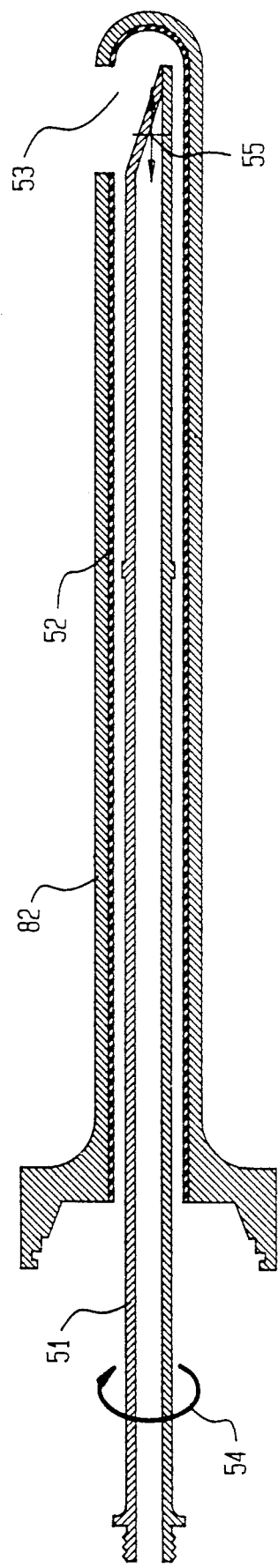
FIG. 5 is a side view, partially in cross-section, of another preferred tip for the aspirator of FIG. 1 which is specifically designed for, use in arthroscopic surgery.

FIG. 5 shows a tip intended for use in arthroscopic surgery. The tip sheath 82 replaces the telescope and its sheath 31 of FIG. 1, and attaches to the outer housing using the identical self-locking taper. In arthroscopic procedures, the telescope is inserted through a separate opening in the knee. A layer of electrical insulating material 52, such as polyurethane, is bonded to the inner diameter of the sheath. To withstand the forces imposed by surgical manipulation of the instrument, sheath 31 is made of metal tubing and, as such, constitutes an electrical conductor. Without insulation, electrocauterizing current, destined for tissue in contact with the end of tip, might flow via tip-sheath contact to unintended anatomy. This insulation may also be present in the sheath shown in FIG. 1. A window in the sheath allows tissue to be drawn into the tip which itself has a bevelled terminus. Material so captured by vacuum applied to the tip bore is then severed by tip rotation 54 and vibration 55. Although FIG. 5 illustrates a bevelled tip, the invention may utilize any of may tips developed for arthroscopic rotating dissectors, including "window" and the "serrated window" configurations shown, for example, in U.S. Pat. No. 4,203,444, and expressly incorporated herein by reference thereto.

The improvement in tissue dissection to be obtained from the present apparatus is illustrated in FIG. 6. The upper row of drawings depict an attempt to dissect tissue using a conventional, non-rotating aspirator tip. At time 0, the vibrating tip enters and begins separating targeted structure. Dissection of a tissue core proceeds at time 1. To sever the segment, the surgeon lifts the tip at time 2 and tries to part the base of the core or pedestal. In doing so, the lower edge of the tip is forced against the base which results at time 3 in release of the entire segment which remains attached to the parent tissue.

A rotating ultrasonic aspirator is shown attempting the same procedure in the lower row of FIG. 6. Again, segment formation occurs at times 0 and 1. The tip then rotates and proceeds with progressive dissection. However at time 2, the pedestal is severed by rotation of the bevelled tip, enabling the tangential component of motion present on edge to complete the dissection, resulting in complete retention of the tissue within the tip at time 3.

The method of providing rotation is not limited to any specific range of speed or direction. For example, the motor may be capable of operating from 0 to 200 rpm (revolutions per minute) or, with appropriate bearings to as much as 3,000 rpm. The direction of rotation may also be reversed without affecting the rate of tissue dissection. In fact, it may be advantageous to periodically reverse rotation when severing certain tissue structures exhibiting asymmetrical morphology that are more easily separated from one side that from the other.

In general, rotation reversed through arcs of from 61 to 360 degrees is found sufficient for most purposes, but rotation through any arc is possible through appropriate control of the motor.

The components of ultrasonic velocity at the working tip of the apparatus are shown in FIG. 9. V is the extensional velocity of the tip surface and is equal to $2\pi f\epsilon$, where f is the frequency of vibration and $\epsilon$ is the peak displacement amplitude. Vn is the component of velocity normal to the edge and is the agent responsible for producing cavitation of intercellular free water. Vt is the tangenital velocity component of the edge whose action is to sever tissue by shear. Vn and Vt are related to V by $$Vn = V \cos\alpha \qquad (3)$$

$$Vt = V \sin\alpha \qquad (4)$$

where $\alpha$ is the bevel angle defined in FIG. 9. When $\alpha$ is 45 degrees, for example, Vn equals Vt. At this angle the cavitational and shearing effects are produced by equal velocities. To Vn and Vt must be added components of the rotational velocity Vr. However, because rotation can not be reversed at rates approaching ultrasonic frequencies, Vr is unidirectional, and not reciprocal, within one cycle of vibration, and therefore does not augment cavitation. The tangential component of Vr does introduce a steady shearing velocity to the tip edge upon which the alternating component, Vt, is superimposed, but the principal function of Vr is to simply ensure that tissue is exposed in its entirety to Vt.

Figure 7:
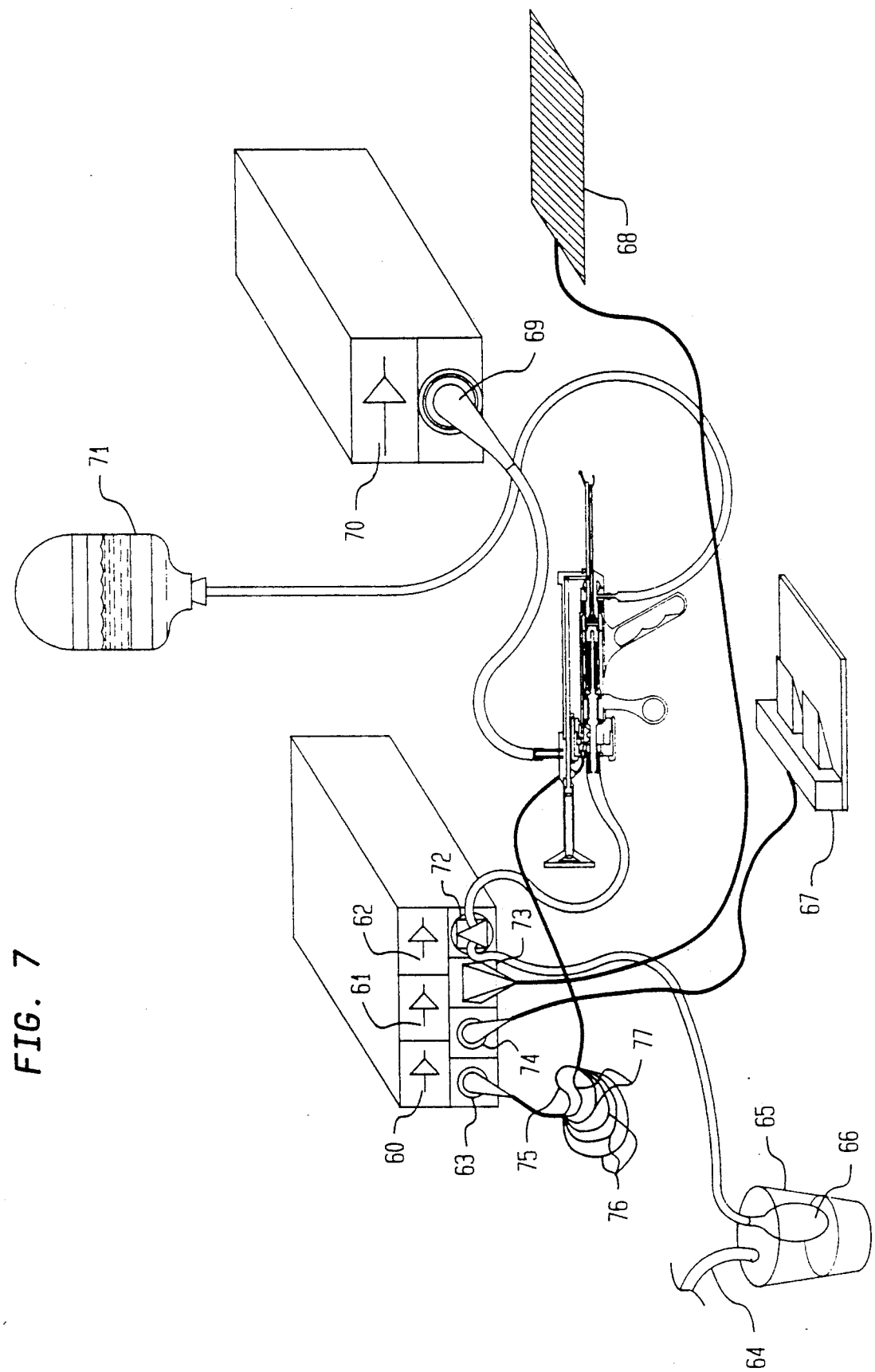
FIG. 7 is a schematic view of the aspirator of FIG. 1 along with related instrumentation prepared for surgery.

The handpiece is shown with its related instrumentation prepared for surgery in FIG. 7. The control unit contains a handpiece connector 63 which supplies appropriate electrical voltages and currents to motor wires 76, ultrasonic transducer lines 77 and electrosurgical conduit 75 from respectively, motor control and speed adjustment 60, ultrasonic generator control and adjustment 61 and electrosurgical generator control and adjustment 62. A footswitch 67, which activates the vibration, rotation and electro-cauterization functions, is also connected to the control unit by connector 74. Electro-cauterizing current is returned through the patient into electrode 68 and thus to the generator via connector 73. A fiber optic illumination source and intensity adjustment 70 is connected to the telescope fitting 23 by cable and connector 69.

Aspiration is accomplished by connection of a vacuum canister 65 to a source of suction 64. This canister contains a specimen trap 66 which communicates directly with tubing entering a pinch valve 72 on the control unit. This valve, when opened, applies vacuum to the aspiration line connected directly to the fitting 24 shown in FIG. 1.

Irrigation is provided from a reservoir 71 suspended at some fixed height above the patient. This canister contains a fluid suitable for performing the procedure. For example, the solution may be glycine for urologic applications, or saline or distilled water for arthroscopic operations. Valve 29 admits or stops the flow of irrigant into the sheath, over the tip and into the surgical site.

In use, the surgeon inserts the sheath 31 into a natural or surgically introduced orifice. He then adjusts irrigation flow by the position of valve 29 or solution reservoir canister height to obtain adequate visibility. Operation of the footswitch in combination with adjustments on the control unit permits vibration amplitude and rotational speed to be selected for optimum tissue dissection rates. Electro-cauterizing current can be applied to the tip as needed again with use of the footswitch. The lower footswitch pedal in FIG. 7 has three positions. The first opens the aspiration pinch valve, the second activates ultrasonic vibration and the third rotates the tip. The upper footswitch pedal controls applications of electro-cauterizing current.

An important feature of the invention is the ability to independently operate all modalities: suction, vibration, rotation, electro-cauterization and tip extension and retraction. The footswitch shown is only one example of a convenient method for combining the separate functions.

Figure 8:
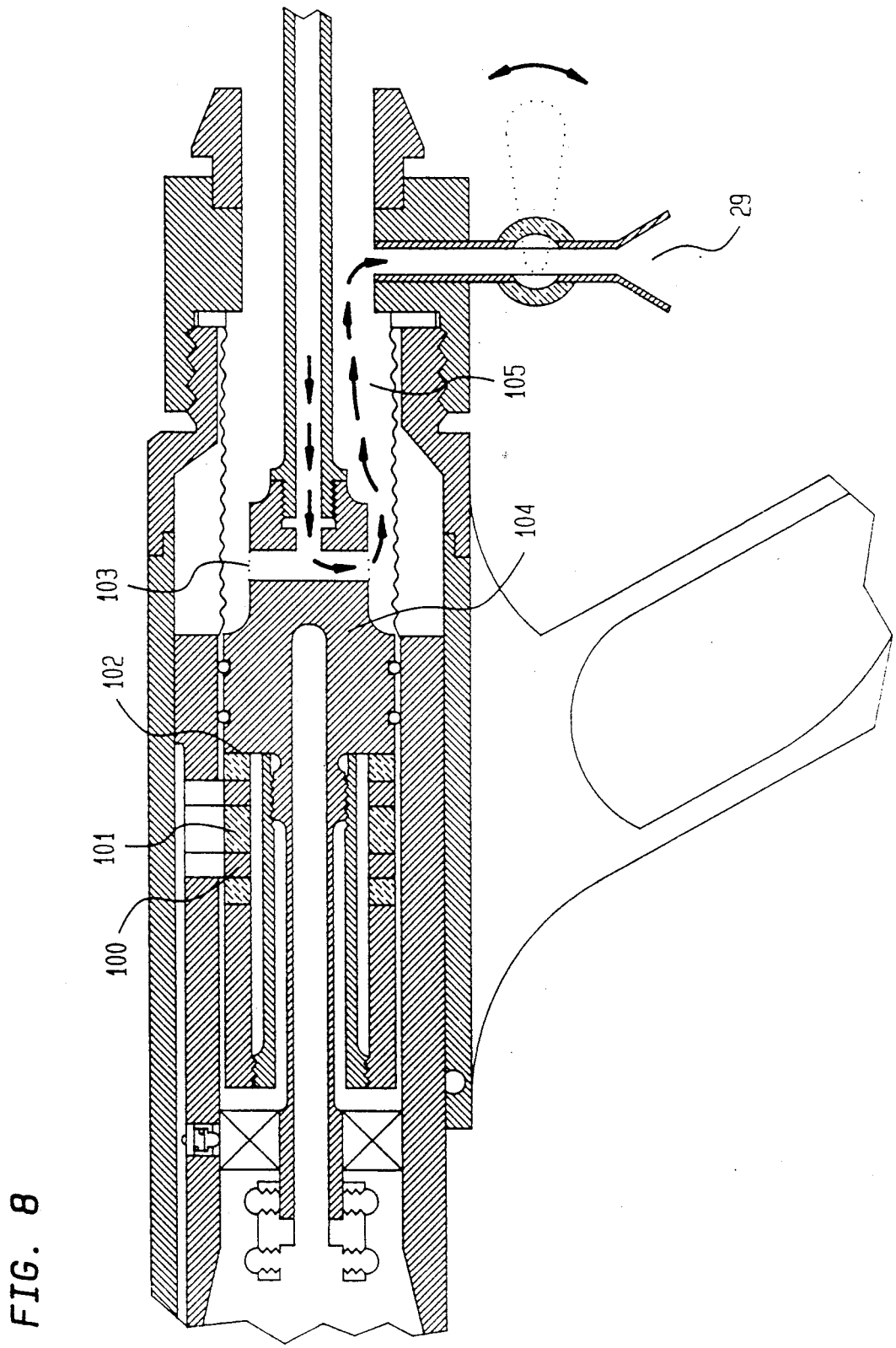
FIG. 8 is a side view, partially in cross-section, of a modification of the aspirator of FIG. 1, whereby aspiration can be conducted through the irrigation port.

It is noted that the invention is not restricted to use of motors with hollow shafts. In some instances, gear trains are fitted to motors that do not have a concentric passageway. By modifying the transducer as shown in FIG. 8, it is possible to aspirate through irrigation port 29 by connecting it to a source of vacuum. The aspiration passage in the transducer, shown continuous in FIG. 2, is terminated 104 in FIG. 8. Dissected tissue proceeds through the tip and encounters cross hole 103 and proceeds 105 to the port.

FIG. 8 also shows an alternative use of piezoelectric material. Rather than a tube, this crystal is a disk 101 whose electrodes are plated on opposite faces. The faces abut metallic rings 100 which are insulated from the rest of the transducer by ceramic spacers 102. The brushes contact these rings and so excite the crystals. In crystals of this type, a voltage applied between the electrodes produces a change in thickness, again exciting extensional vibration.

The size of the sheath is preferably about 29 french for passage through most natural body openings. Also, this relatively small size allows surgeons to create smaller surgical openings when the device is to be used for application in knee surgery, for example. The present apparatus is ideally suited for cutting meniscus in artroscopic procedures.

FIGS. 10-12 illustrate the use of a motor externally connected to the handpiece through a flexible cable which rotates the ultrasonic transducer. The cable itself 111 consists of a flexible, but stationary, conduit 113 for confining and protecting a flexible shaft 112 preferably made of multi-stranded wire which is capable of transmitting rotation through the curved path defined by the conduit.

The conduit is releasbly connected at one end to the motor housing and at its other end to the handpiece rear bulkhead 146 by means of a retaining collar 115, cemented or otherwise permanently attached to the conduit, sandwiched between a nut 114 and the housing.

Outside of the handpiece, the flexible shaft is connected to the armature of the motor. This cable enters the handpiece through the conduit and is terminated in the pin engagement shown as 116. This engagement contains a pin 117 whose shape is square, rectangular, oval or of a shape that when inserted into a mating cavity 116 communicates rotation to the insulated coupling 121, while allowing for relative axial displacement of the pin and cavity. The chuck, which contains the cavity, is supported on bearings 120 which accommodate thrust and other forces produced by flexure of the cable upon the engagement. Since the pin is free to slide axially within the cavity, the ultrasonic transducer and tip may be displaced axially by operating the thumb and finger trigger while rotation is maintained by the motor.

With the exception of coaxial aspiration, all previously mentioned functions of the device are preserved in this embodiment. Because sterile fluids and tissue are aspirated by the tip and their sterility under conveyance to a collection vessel must be maintained, aspiration is performed in the device of FIG. 10 through a cross hole in the transducer union whose function is illustrated in detail FIG. 8. Thus in FIG. 10, the stem of the transducer is shown as a solid.

While it is apparent that the invention herein disclosed is well calculated to fulfill the objects above stated, it will be appreciated that numerous modifications and embodiments may be devised to those skilled in the art. and it is intended that the appended claims cover all such modifications and embodiments as fall within the true spirit and scope of the present invention.

What is claimed is:

1. A surgical instrument comprising:
    a handpiece;
    a vibration source within the handpiece for generating mechanical vibrations in response to current applied thereto;
    elongated tool means operatively associated with said vibration source and attached to said handpiece at a point where essentially no vibrational motion occurs, said tool means extending away from said handpiece to a work site, whereby vibration of said tool means causes disintegration and removal of hydrated biological material;
    means connected to said vibration source at said point where essentially no vibrational motion occurs, for rotating said vibrational source and said elongated tool means about their circumference through at least one revolution; said rotating means enabling said elongated tool means to remove non-hydrated biological material;
    means for irrigating said work site with fluid to assist in withdrawing removed biological material therefrom; and
    aspiration means for withdrawing irrigation fluid and removed biological material from said work site;
    wherein the elongated tool means has a length of $\Gamma/4 + n\,\Gamma/2$ where n is 0 or a positive integer and $\Gamma = c/f$ where f is the frequency of operation and c is the velocity of extensional waves in said tool means.

2. The instrument of claim 1 wherein said elongated tool means includes a bevelled tip for providing increased shearing of biological material.

3. The instrument of claim 1 further comprising a stationary sheath for surrounding said elongated tool means, said sheath including a closed tip portion having at least one aperture spaced therefrom to form a window in said sheath which facilitated further removal of biological material.

4. The instrument of claim 1 further comprising a support structure located within said handpiece for mounting said vibration source and rotating means and capable of independent longitudinal movement relative to said handpiece.

5. The instrument of claim 4 wherein said vibration source includes a tubular piezoelectric crystal having electrodes on inner and outer surfaces thereof; a union for connecting said crystal to said elongated tool means; and a stem extending towards said rotating means.

6. The instrument of claim 5 wherein said rotating means comprises a motor for generating rotational forces and means for transmitting said forces to said vibration source stem and to said elongated tool means for rotation thereof.

7. The instrument of claim 6 wherein the stem has a length which is not resonant at the operating frequency of the crystal.

8. The instrument of claim 1 wherein said vibration source includes a piezoelectric disk having electrodes on opposite faces thereof.

9. The instrument of claim 1 further comprising an elongated sheath for surrounding said elongated tool means and including an opening to exposure said elongated tool means to the biological material to be removed.

10. An endoscopic ultrasonic aspirator comprising the surgical instrument of claim 1 and further comprising means for viewing said work site from said handpiece.

11. The aspirator of claim 10 wherein said viewing means further comprises means for illuminating said work site to facilitate viewing thereof.

12. The aspirator of claim 11 further comprising an elongated sheath for surrounding said elongated tool means and wherein said viewing means is located within said sheath.

13. The aspirator of claim 12 wherein said sheath includes a hood member at the forward end thereof to assist in obtaining an unobstructed view of the work site through said viewing means.

14. The instrument of claim 11 wherein said vibration source includes a piezoelectric crystal, a union for connecting said crystal to said elongated tool means, and a stem.

15. The instrument of claim 14 wherein said piezoelectric crystal is electrically insulated from said union and stem, and further comprising means for energizing said elongated tool means to supply current for cauterizing biological material that is not removed.

16. A surgical instrument comprising:
    a handpiece;
    a vibration source within the handpiece for generating mechanical vibrations in response to current applied thereto, said vibration source including a piezoelectric crystal, a union for connecting said crystal to an elongated tool means, and a stem;
    elongated tool means operatively associated with said vibration source and attached to said handpiece at a point where essentially no vibrational motion occurs, said tool means extending away from said handpiece to a work site, whereby vibration of said tool means causes disintegration and removal of hydrated biological material;

means connected to said vibration source for rotating said vibration source and said elongated tool means about their circumference through at least one revolution, said rotating means enabling said elongated tool means to remove non-hydrated biological material;

means for irrigating said work site with fluid to assist in withdrawing removed biological material therefrom; and aspiration means for withdrawing irrigation fluid and removed biological material from said work site; and means for electrically insulating each of piezoelectric crystal and said rotation means from said stem and union.

17. The instrument of claim 16 wherein said insulating means comprising ceramic spacers and further comprising means for energizing said elongated tool means to supply current for cauterizing biological material that is not removed.

18. The instrument of claim 17 wherein said energizing means comprises a spring member connected to a current source and contacting said stem through bearing means.

19. A surgical instrument comprising:

a handpiece;

a vibration source within the handpiece for generating mechanical vibrations in response to current applied thereto;

elongated tool means operatively associated with and vibrated by said vibration source and attached to said handpiece at a point where essentially no vibrational motion occurs, said tool means extending away from said handpiece to a work site, whereby vibration of said tool means causes disintegration and removal of hydrated biological material;

means connected to said vibration source for rotating said vibration source about its circumference through at least one revolution, said rotating means enabling said elongated tool means to remove non-hydrated biological material;

a support structure located within said handpiece for mounting said vibration source and capable of independent longitudinal movement relative to said handpiece;

means for longitudinally reciprocating said support structure and elongated tool means towards and away from said work site while said tool is vibrating independently of moving said handpiece;

means for irrigating said work site with fluid to assist in withdrawing removed biological material therefrom; and aspiration means for withdrawing irrigation fluid and removed biological material from said work site.

20. A surgical instrument comprising:

a handpiece;

a vibration source within the handpiece for generating mechanical vibrations in response to current applied thereto;

elongated tool means operatively associated with and vibrated by said vibration source and attached to said handpiece at a point where essentially no vibrational motion occurs, said tool means extending away from said handpiece to a work site, whereby vibration of said tool means causes disintegration and removal of hydrated biological material;

means connected to said vibration source at said point where essentially no vibrational motion occurs, for rotating said vibration source about its circumference through at least one revolution;

means for longitudinally reciprocating said support structure and elongated tool means towards and away from said work site while said tool is vibrating independently of moving said handpiece;

means for irrigating said work site with fluid to assist in withdrawing removed biological material therefrom; and aspiration means for withdrawing irrigation fluid and removed biological material from said work site.

21. The instrument of claim 20 wherein the rotating means is capable of rotating the elongated tool means in either clockwise or counterclockwise directions.

22. A surgical instrument comprising:

an elongated hollow tool for applying mechanical vibrations to a work site;

means for withdrawing fluid or material from the work site through the tool;

a handpiece having first and second ends with a first opening defining by the first end wherein the tool extends from the first opening to the work site;

a vibration source within the handpiece for generating mechanical vibrations in response to electrical current applied thereto, wherein the vibration source is operatively associated with the tool for transmitting vibrations thereto and wherein the tool is attached to the handpiece at a point where no vibration occurs; and means connected to said point where no vibration occurs for rotating the vibration source and the tool while the tool is vibrating to apply the mechanical vibrations to the work site while also applying shearing forces thereto.

23. The instrument of claim 22 wherein the includes a bevelled tip for providing increased shearing of material at the work site.

24. The instrument of claim 22 wherein the withdrawing means includes an aspirator comprising means for irrigating the work site with fluid and means for removing fluid by suction or vacuum.

25. The instrument of claim 22 further comprising means for insulating said vibration source from said tool, and means for energizing said elongated tool means to supply current for cauterizing the work site.

26. The instrument of claim 22 further comprising an elongated sheath for surrounding said tool and means for viewing said work site located within said sheath.

* * * * *